United States Patent [19]
Canter et al.

[11] Patent Number: 6,060,547
[45] Date of Patent: May 9, 2000

[54] FILM FORMING FOUNDATION

[75] Inventors: Marcia Lang Canter, Hamilton; Brian Dale Barford, West Chester, both of Ohio; Brian David Hofrichter, Owings Mill, Md.

[73] Assignee: The Proctor & Gamble Company, Cincinnati, Ohio

[21] Appl. No.: 08/430,961

[22] Filed: Apr. 28, 1995

[51] Int. Cl.$^7$ .................................................. C08K 5/10
[52] U.S. Cl. .......................... 524/280; 523/105; 523/122; 524/377; 524/388; 524/767; 524/801; 424/63; 424/69; 424/401; 424/70.12; 424/70.15; 424/70.16; 424/70.11; 514/63; 514/772.3; 514/772.5
[58] Field of Search ...................... 524/280, 377, 524/388, 467, 801; 523/105, 122; 514/63, 772.3, 772.5; 424/63, 69, 401, 70.12, 70.15, 70.16, 70.11

[56] References Cited

U.S. PATENT DOCUMENTS

| | | | |
|---|---|---|---|
| 4,427,811 | 1/1984 | Elias et al. | 524/96 |
| 4,599,372 | 7/1986 | Bardoliwalla et al. | 524/388 X |
| 4,743,648 | 5/1988 | Hill et al. | 524/801 X |
| 4,839,163 | 6/1989 | Busch, Jr. | 424/63 |
| 5,055,500 | 10/1991 | Peters | 523/319 |
| 5,061,481 | 10/1991 | Suzuki et al. | 424/63 |
| 5,143,671 | 9/1992 | Peters et al. | 264/117 |
| 5,143,722 | 9/1992 | Hollenberg et al. | 424/63 |
| 5,145,898 | 9/1992 | Narula et al. | 524/310 |
| 5,162,378 | 11/1992 | Guthauser | 514/785 |
| 5,169,881 | 12/1992 | Peters et al. | |
| 5,196,187 | 3/1993 | Nicoll et al. | 424/70 |
| 5,216,033 | 6/1993 | Pereira et al. | 514/844 |
| 5,216,070 | 6/1993 | Plochocka et al. | 524/377 X |
| 5,218,039 | 6/1993 | Stoy et al. | 524/388 X |
| 5,234,682 | 8/1993 | Macchio et al. | 424/69 |
| 5,260,052 | 11/1993 | Peters et al. | 424/63 |
| 5,266,322 | 11/1993 | Myers et al. | 424/41 |
| 5,288,481 | 2/1994 | Ounanian et al. | 424/63 |
| 5,362,482 | 11/1994 | Yoneyama et al. | 424/69 |
| 5,412,004 | 5/1995 | Tachibana et al. | 524/27 |
| 5,500,148 | 3/1996 | Ohba et al. | 524/502 |
| 5,567,426 | 10/1996 | Nadaud et al. | 524/501 |

FOREIGN PATENT DOCUMENTS

| | | |
|---|---|---|
| 0530084A1 | 8/1992 | European Pat. Off. . |
| 0600445A2 | 6/1994 | European Pat. Off. . |
| 0612517A1 | 8/1994 | European Pat. Off. . |
| 61-158913 | 7/1986 | Japan . |
| WO93/14742 | 8/1993 | WIPO . |
| WO93/24098 | 12/1993 | WIPO . |

OTHER PUBLICATIONS

Elliot, T. J. "More durable make–up based on pigmented water–on–solvent emulsions", *International Journal of Cosmetic Science*, vol. 1, pp. 17–25 (1979).

Barabas, E. S. (Abstract) "N–Vinyl Amide Polymers", *Encyclopedia of Polymer Science and Engineering*, 2nd. Ed. vol. 17, pp 198–257, 1988.

CTFA Cosmetic Polymers, Dremacryl Lt for Skin Care Formulations, (Technical Brochure).

Skin Care Formulating Guide for Dermacryl Film Forming Polymers, National Starch and Chemical Company, (Technical Brochure).

Material Safety Data Sheet, Air Products and Chemicals, Inc.

Eastman AQ Polymers Properties and Applications, Eastman Chemical Company.

Porter, S. N. "Two–in–One Raw Materials. Water Dispersible Pigments for Dual–Functional Liquid Makeup", *Cosmetics & Toiletries*, vol. 108, pp. 87–92, 1993.

CAPLUS Abstract: German DE3017017, Nov. 20, 1980.

CAPLUS Abstract: Japan Jp05017320, Jan. 26, 1993 (document not available).

Derwent, Abstract of European Patent Application: EP206671, Dec. 30, 1986.

Derwent, Abstract of Japanese Patent Application: JP03079669, Apr. 4, 1991.

Derwent, Abstract of European Patent Application: EP388582, Sep. 26, 1990.

Derwent, Abstract of Japanese Patent Application: JP06239718A, Aug. 30, 1994.

Derwent, Abstract of Japanese Patent Application: KJP01203313A, Aug. 16, 1989.

Derwent, Abstract of Japanese Patent Application: JP54151139A, Nov. 28, 1979.

*Primary Examiner*—Judy M. Reddick
*Attorney, Agent, or Firm*—Darryl C. Little; Loretta J. Henderson

[57] ABSTRACT

The invention is a water-in-oil emulsion film forming foundation having a synergistic combination of about 0.5% to about 10% by weight of a water soluble or water dispersible film forming polymer, as well as about 0.5% to about 35% by weight of the composition of one or more plasticizing solvent(s). Both the polymer and solvent(s) combined together in the aqueous phase are in a cosmetically acceptable carrier providing suitable feel and appearance during application, as well as excellent wear and appearance benefits after application. Yet this film forming foundation provides a flexible, light feel that resembles other foundations, and is easily removed with soap and water.

18 Claims, No Drawings

FILM FORMING FOUNDATION

FIELD OF THE INVENTION

This invention relates to polymer containing, film forming, improved wear foundations, which are easily removed with soap and water.

BACKGROUND

One of the major purposes of skin cosmetics is to improve the outward, especially facial, appearance. Typically foundations are used to enhance features, or mask perceived imperfections in them. As foundations are typically applied prior to other color cosmetics, they provide a uniform base of color and coverage which improve the overall appearance of make-up. Characteristics considered by consumers when choosing a foundation fall into three general areas; look (or appearance both upon application and after wear), feel (e.g., ease of application and the feel of the "made up" area), and wear (resistance to water, oil, abrasion, etc.). These foundations are generally available in the form of liquid, semi-liquid or cream suspensions, emulsions, gels, as well as pressed powders or anhydrous oil and wax compositions.

The skin cosmetic art has long sought to provide foundations that alter the perception of the skin, especially the skin of the face. For example, foundations are used over the entire face to mask perceived imperfections in skin texture, pigmentation or vascularization. Foundations present special challenges to the skilled artisan as they cover larger areas of the skin, thus defects are more apparent, making it more difficult to provide a good look. Unlike other color cosmetics, they are typically applied with the hand, and their presence is more visibly apparent than other skin cosmetics, such as moisturizers. As a result, the foundation must provide an exceptionally even covering, without looking unnatural, and must be easy and pleasant feeling to apply.

Usually the consumer chooses foundations that provide the desired skin color. These needs are often met by selecting the properly pigmented foundation to provide the desired effect.

The skin cosmetic industry strives to produce long wearing, good looking foundations to hide perceived imperfections in facial skin. These foundations are prepared from a number of known materials. However, the commonly used materials present problems in that they are not impervious to the effects of the water or skin secretions, including sweat or sebaceous oils and thus they do not wear well. Such penetrability provides for "bleeding" of the foundation, and its concomitant uneven look when worn for a long period of time, "smudging" or abrasion of the foundation, and the like. Thus a foundation must be substantial enough to withstand these common signs of wear.

As an example of this effort to improve the wear characteristics, the art has considered formulating simple pigment mixtures of volatile solvents with waxes and gelling agents. These compositions are not easy to pleasant to apply, and may use costly solvents, making the foundation more expensive. While such formulations may provide water resistant films, employing volatile organic solvents in products has provided compositions that lacked spreadability. Packaging problems occurred because the loss of solvent in the product before application produced a hard, unusable material. In addition, these pigmented mixtures have not been successful because they require careful application to avoid heavy coverage.

To avoid these stability and application problems, conventional pigmented oil-in-water emulsions were developed. They are cheaper, and tend to be relatively stable. The pigmented oil-in-water emulsion is one of the more popular types of foundations on the market today. The pigmented oil-in-water emulsion lends itself to variation in pigment level and oil level to give different degrees of color coverage and emolliency. However, these foundations have several drawbacks: First, because such a foundation is not impenetrable to oil and water, partial 'fading' or 'bleeding' of the color during wear still occurs. Second, while these foundations may be easier to apply, they can still lack blendability. Lack of blendability is a considerable problem as the cosmetic cannot be touched-up, and typically the make-up must be removed and applied anew. Third, because the external phase is aqueous, these foundations can produce a cold and wet feeling upon application. Fourth, they can be difficult to spread evenly on the skin, particularly when oily substances (for example, previously applied moisturizers, sebum, etc.) are present on the skin during application.

Conventional foundations do not produce coverage which is sufficiently water-resistant, oil-resistant, and friction-resistant. Those in the art have sought to improve foundations' wear properties, such as adhesion to the skin, resistance to abrasion, water, and skin oils, by providing a foundation that forms a film. Often this "film" is a wax or polymer, that is packaged with solvent, as described above. Upon evaporation the foundation leaves a paste or continuous film on the face. This foundation typically feels different during application and wear then conventional skin cosmetics. This difference in feel has resulted in poor consumer acceptance of these products.

A more recent strategy employed by the art to address this problem is the coating of pigments in skin cosmetics. It is thought that such coated pigments may stay in suspension better, and provide color stability in the package. Examples of hydrophobically coated pigments and hydrophilically treated pigments are known. Incorporation of these pigments into an cosmetic may improve wear characteristics. These products do not form a fully integrated film, but have slightly improved wear because the coating on the pigment can adhere to the skin. For example, U.S. Pat. No. 5,260,052 discloses the use of polymer coatings for this purpose.

The most recent development in the art is the advent of "film forming" skin cosmetics. The goal of a "film forming" skin cosmetic is to provide the better looking, longer lasting benefits compared to the conventional skin cosmetic, while avoiding a film that appears or feels heavy or drying to the skin. Attempts to address the problems of the conventional skin cosmetic have led to previously unforeseen problems, such as giving an undesirable "plaster-like" look to the skin, the skin cosmetic "peeling up" from the face, cracking, peeling, or flaking after wear. Abrasion by the hands or clothes has often exacerbated this cracking, peeling or flaking.

Should these problems be overcome, these skin cosmetics offer challenges to consumer acceptance in the feel or the application of the skin cosmetic. Because consumers have become accustomed to the dry, smooth feel of the conventional non-film forming skin cosmetics, the different feel and often different application techniques of the film forming skin cosmetics are not readily received by consumers. For example, because these film forming skin cosmetics thicken rapidly while forming the film, they may be difficult to apply and then feel tacky at the end of application, or if applied too slowly they may provide a streaky or uneven appearance, as new applications of the cosmetic do not blend well with previously applied and partially dried skin cosmetic. Additionally, the film forming skin cosmetics may not spread as well because they may be forming the film or thickening during application.

As a result of these challenges, the art has avoided liquid, semi-liquid or cream formulations of film forming skin cosmetics, such as foundations, because they are applied with the hands. As an example, the undesirable thickening or tackiness would be most noticeable in the application of a foundation. In addition, any tackiness or thickening would exacerbate the problems of blending the foundation.

However, the challenges remain for foundations applied or manipulated by the hands, especially when used over larger areas. For example, external phase polymers in skin cosmetics feel tacky during application and polymer coated pigments can lack the "evenness" desired, when applied to a large area. In addition, where the polymers used are hydrophobic, they are also difficult to wash off, without special aids, such as cleansing creams and the like. Each of these approaches provide new undesirable application and "feel" drawbacks. Of course, improvements found in formulating these polymers would be desirable.

The art has also sought new polymers in an effort to avoid these drawbacks. The art teaches several film forming polymers, which are said to be safe for skin:

One such film former is a water dispersible acrylic, manufactured by various suppliers under various names, such as DERMACRYL LT, (Acrylates/Octylacrylamide Copolymer) from National Starch. This polymer is water soluble, and thus is expected to provide ease in formulation. However, soluble polymers in general not provide the same "skin cosmetic" feel as non-filming skin cosmetics, and tends to be sticky during drying. While consumers may tolerate this in products where extended wear is the overriding concern, but such products generally do not enjoy wide consumer acceptance in skin cosmetics for this reason.

Polyester AQs, are water dispersible sulfopolyester. Eastman's U.S. Pat. No. 5,260,052 describing pigment dispersions using a sulfopolyester as a pigment coating, with Eastman's U.S. Pat. No. 5,226,322 describing a composition comprising an oil-in-water emulsion of polyester resin for skin cosmetic purposes with AQ. Several of these resins exist, for example, AQ29D, AQ35S, AQ38D, AQ38S, AQ48S, AQ55S, and are available from Eastman Chemicals. They are marketed either as solid or dispersed polymers. Typically, skin cosmetics formulated from these polymer coated pigments of from oil-in-water emulsions containing these polymers provide skin cosmetics that are tacky and are not generally used or widely recommended where the foundation is applied with the hands.

Several other polymers exist in the art that are touted as being useful for skin cosmetics, but lack the preferred characteristics, such as low tackiness, good skin adhesion and the like.

It would be advantageous to provide a film forming skin cosmetic that is stable, easy and pleasant feeling to apply, provides a good looking cosmetic, and also provides good wear characteristics. Yet the cosmetic must be easily removed with soap and water.

Thus the desired film forming foundation provides the proper "feel" in that it lacks tackiness or stickiness, does not thicken too rapidly during application, but is smooth and dry, while adhering to the skin. The desired film forming foundation also provides a "good look" even coverage, is blendable and adheres to the skin, while not appearing heavy. The desired film forming foundation is not compromised by skin secretions or water, does not "bleed" with wear, does not crack, smudge, abrade or peel.

SUMMARY OF THE INVENTION

We have developed a novel film forming foundation composition providing superior feel, look and wear characteristics. This water-in-oil emulsion foundation provides a synergistic combination of about 0.5% to about 10% by weight of water compatable film forming polymer, as well as about 0.5% to about 35% by weight of plasticizing solvent in the aqueous phase. This foundation provides for suitable feel and appearance during application, as well as excellent wear and appearance benefits after application. Yet this film forming foundation provides a flexible, light feel that resembles other foundations, and is easily removed with soap and water.

DETAILED DESCRIPTION OF PREFERRED EMBODIMENTS

This novel foundation provides surprising benefits over the prior art, measured by attributes which define an acceptable foundation. Attributes that can be specifically tailored for a cosmetic, such as color, viscosity and the like, are not further discussed. However, attributes which are inherent to the formula of the foundation, such as lack of tackiness, blendability, spreadability and the like, provide an early measure of the consumer acceptance. Thus, attributes are used herein to illustrate the invention's advantages over the art. These attributes typically fall into the three areas discussed previously. First, the "look," primarily the evenness, and blendability. Second, the "feel," primarily the spreadability, slipperiness, playtime, residue and tackiness. Finally, the wear properties, as evidenced by the water, oil and abrasion resistance, retention of the "freshly applied" look, shine, control, original color (lack of "bleeding" of color over time), flawlessness, and lightness on the skin over time. The foundation and its advantages will be further discussed as this description proceeds.

Because it can take up to 2 minutes for the average consumer to apply a foundation and because of the large surface area (typically >200 $cm^2$) of the face, we have striven to provide a foundation that can be easily blended, or even overcoated after 2 minutes, without significant thickening or tacky feeling.

As used hereinafter, the term "foundation" refers to a liquid or semi-liquid skin cosmetic which includes, but is not limited to lotions, creams, gels, pastes, and the like. Typically the foundation is used over a large area of the skin, such as over the face, to provide a particular look. As used hereinafter, the foundation is a water-in-oil emulsion formulation, preferably a water-in-silicone emulsion formulation. Thus when the "emulsion" is discussed, it is understood to describe the formulation of the foundation. Typically, for the purposes of this disclosure, the term "emulsion" or "film forming foundation emulsion" will appear in discussions directed to formulation details of the foundation composition.

It is well understood by the skilled artisan that a water-in-oil emulsion has hydrophylic or aqueous material dispersed in hydrophobic or "oil"-like material. Thus the internal or dispersed phase is aqueous or "water"-like in nature and is called the "aqueous phase." The external or continuous phase is hydrophobic, and is called the "oil phase."

The foundation contains a film forming polymer/plasticizing solvent in the aqueous (internal) phase of the emulsion. This minimizes the unpleasant tacky sensation characteristic of polymers on the user's hands and fingers during the cosmetic's application. The combination of aqueous phase polymer and solvent is chosen to provide proper evaporation rate and polymer solvation for extension of the workability of the foundation and delay of any perceived onset of tackiness until after application is complete. Thus the judicious choice of plasticizing solvent, based upon the film forming polymer and evaporation rate, allows for the perceived tackiness to remain substantially imperceptible until the material has formed a film.

Typically, the pigment is presented in the oil phase to provide even coverage during initial application of the foundation.

All amounts specified herein are by "weight percent", unless otherwise specifically stated. Thus when specifying a non-solid ingredient, the amount is not in standard liquid measure. The skilled artisan is quite capable of converting between the weight percent and the appropriate weight or volume to prepare a finished formulation. In addition, some materials are specified as weight percent of both the specific phase (i.e., the oil or aqueous phase) and weight percent for the composition as a whole. This extra information is provided to guide the artisan in preparing the formulation.

The aqueous phase of the emulsion is comprised of the film forming polymer, the plasticizing solvent, water soluble additives, and the like. Preferably water can comprise up to about 60% by weight of the foundation composition. It is more preferred that water is present in the overall composition of the foundation in an amount of about 10% to about 50% by weight.

The oil (external) phase may comprise branched paraffins, hydrocarbons, esters, ethers, silicones and the like. Preferably the oil phase is comprised of volatile material and contains no "oils" as defined by the C.T.F.A. Cosmetic Ingredient Handbook 3rd Ed., Cosmetic and Fragrance Assn., Inc., Washington D.C. (1982). incorporated herein by reference. More preferably, the oil phase comprises silicones, more preferably up to 90% of the oil phase is volatile silicones, non-volatile silicones and mixtures thereof. Still more preferably, these silicones are chosen from cyclomethicones and dimethicones and mixtures thereof. These materials are known in the art and are often commercially available. Thus one of the most preferred oil phases can be considered, and is thus defined as a "silicone" phase and thus the foundation is defined as a "water-in-silicone" emulsion.

In the "water-in-silicone" emulsion embodiment, a silicone is used in the oil phase and the silicone can comprise one or more volatile silicones, non-volatile silicones, and mixtures of volatile silicones and non-volatile silicones. The silicone is present in an amount of from about 1% to about 50% by weight of the composition. Suitable volatile silicones include cyclic and linear volatile polyorganosiloxanes (as used herein, "volatile" refers to those materials which have a measurable vapor pressure at ambient conditions). A description of various volatile silicones is found in Todd, et al. "Volatile Silicone Fluids for Cosmetics", 91 *Cosmetics and Toiletries* 27–32 (1976). Preferred volatile silicones can include cyclic and linear polydimethylsiloxanes.

The volatile linear silicones generally have viscosities of less than about 5 centistokes at 25° C., while the volatile cyclic silicones typically have viscosities of less than about 10 centistokes. Some examples of volatile silicones useful in the present invention include: DOW CORNING'S 344, 345, 244, 245, AND 200 silicones (manufactured by the Dow Corning Corporation): SILICONE 7207 and SILICONE 7158 (manufactured by the Union Carbide Corporation). SF1202 (manufactured by General Electric), SILOXANE 5223 (available from Wacker Silicones) and the like. Of course, others are available and known in the art.

Suitable non-volatile silicones preferably have an average viscosity of from about 10 to about 2,000,000 centistokes at 25° C., more preferably from about 10 to about 50,000 centistokes, even more preferably from about 50 to about 5000 centistokes. Of course, higher viscosity non-volatile silicone conditioning agents can also be used. Suitable non-volatile silicone fluids include, for example, polyalkyl siloxanes, polyaryl siloxanes, polyalkylaryl siloxanes, polysiloxanes with amino functional substitutions, polyether siloxane copolymers, and mixtures thereof. Preferred non-volatile siloxane fluids that may be used include, for example, polydimethylsiloxanes, polymethylphenylsiloxanes polyalkyl siloxanes and polyether siloxane copolymers and the like. These siloxanes are available, for example, from Dow Corning, as the DOW CORNING 200 SERIES DOW CORNING DC-1248, DOW CORNING DC-593, 556 COSMETIC GRADE FLUID DOW CORNING 2502 or from the General Electrical Company, as SF 1075 methyl phenyl fluid, SF1202 and the like. References disclosing suitable silicone fluids include U.S. Pat. No. 2,826,551; U.S. Pat. No. 3,964,500; U.S. Pat. No. 4,364,837, incorporated herein by reference. In addition, *Silicone Compounds* distributed by Petrarch Systems Inc., 1984 provides an extensive (although not exclusive) listing of suitable silicon fluids. Other suitable and preferred silicones are disclosed in U.S. Pat. No. 5,143,722, incorporated herein by reference.

This oil phase can additionally comprise oil soluble substituents, such as colorants or pigments, emollients, fragrances, waxes, stabilizers, and the like.

The Film Forming Polymer

The film forming polymer used in the composition of the invention is compatible with the aqueous phase of the emulsion, and is incorporated in the internal phase of the water-in-oil emulsion, rather than in simple solution or in an oil-in-water emulsion. The polymer can be water dispersible, or water soluble, but is not a cross linked or a water swellable polymer. Of course, the polymer must be capable of forming a thin elastomeric film that physically adheres or interacts with the skin. The polymer film, when formed must also be water removable, that is easily removable with water and soap. It is preferred that the polymer be chosen so as not to be tacky.

The film forming polymer is formulated in the aqueous phase of the emulsion. The polymer is selected to provide a finished foundation preferably with a glass transition temperature (Tg) of about room temperature to about body temperature. "Glass transition temperature" or "Tg" refers to the temperature where the polymer softens or transitions from brittle to plastic, in the absence of plasticizers. This provides for a flexible polymer during application and wear. When the Tg is too high, the foundation may be hard to apply, and may flake. If it is too low, the foundation will be less adhesive (and perhaps more cohesive) and will tend to "ball up" on application.

Of course, the Tg of the polymer itself can vary. For example, it is expected that polymers with Tg of up to about 60C or higher are useful, provided the finished formulation has the proper Tg. For example polyvinylpyrrolidinone is thought to have a Tg greater than 90C, but is useful in the invention. Typical polymers used in the invention are thermoplastic, rather than thermosetting.

Additionally, the polymer should be selected to provide an aqueous phase that is fluid enough to be handled and reasonably incorporated into the final emulsion composition as the dispersed or internal phase. Gelled and extremely viscous solutions can be used, but may impact ease of incorporation or final viscosity. Thus it is preferred to select polymers which can be added at levels to derive film forming and extended benefits, while maintaining workability of the final aqueous phase.

Examples of preferred polymers that have acceptable Tg, skin adhering properties and viscosity include, sulfopolyester resins, such as AQ sulfopolyester resins, such as AQ29D, AQ35S, AQ38D, AQ38S, AQ48S, and AQ55S (available from Eastman Chemicals), Vinex resins, such as VINEX 2034, VINEX 2144, and VINEX 2019 (available from Air Products), Dermacryl acrylic resins (available from National Starch), polyvinylpyrrolidinones (PVP), including LUVISKOL K17, K30 and K90 (available from BASF), water soluble copolymers of PVP, including PVP/VA S-630 and W-735 and PVP/dimethylaminoethylmethacrylate Copolymers such as COPOLYMER 845 and COPOLYMER 937 available from ISP, and the like. Most preferred polymers include AQ38S and PVP. Typically the polymer is present in levels of from about 0.5% to about 10% by weight. More preferably, the polymer lever is from about 1% to about 8% by weight.

Using the parameters defined above, and depending upon the choice of polymer, the preferred level of the polymer may vary. For example, when PVP is used as the film forming polymer, a still more preferred level is from about 1% to about 5% by weight. As another example, when the sulfopolyester AQ38S is used, the still more prefered level is from about 2% to about 8% by weight.

As used herein, the term "sulfopolyester resins," "sulfopolyester resin" or "AQ resin" refers to any of the AQ sulfopolyester resins, such as AQ29D, AQ35S, AQ38D, AQ38S, AQ48S and AQ55S, available from Eastman Chemicals, as described above.

As used herein, the term polyvinylacetate/polyvinyl alcohol polymer refers to such polymers as they are known in the art. Preferred examples of these are referred to as "Vinex" or "Vinex resins", available from Air Products, such as VINEX 2034, VINEX 2144, and VINEX 2019 described above.

As used herein the term water dispersible acrylic resins refers to those polymers as they are known in the art. "Dermacryl" is a preferred family of such acrylic polymer resins, available from National Starch, as DERMACRYL LT and the like.

As used herein PVP refers to polyvinylpyrrolidones as they are known in the art. Their description, characterization and commercial designations is disclosed by E. S. Barabas in the *Encyclopedia of Polymer Science and Engineering*, 2 Ed. Vol. 17 pp. 198–257.

The Plasticizing Solvent

The term "plasticizing solvent," as used herein includes slow evaporating, water miscible or dispersible cosolvents that are 1) generally recognized as safe (GRAS), many of these are listed in C.T.F.A. Cosmetic Ingredient Handbook, 3rd Ed., Cosmetic and Fragrance Assn., Inc., Washington D.C. (1982) pp. 575–580, incorporated herein by reference, or 2) include slow evaporating glycols and glycol ethers including for example, propylene glycol, butylene glycol, hexylene glycol, glycerine, dipropylene glycol, dipropylene glycol methyl ether (commonly known as DPM), propylene glycol phenyl ether, and polyethylene glycols (PEGs) such as PEG 4 and PEG 8, other classes of solvents include, propylene carbonate, and dimethyl isosorbide and mixtures thereof. More preferred solvents include propylene glycol, butylene glycol, propylene carbonate, dimethyl isosorbide and mixtures thereof. These solvents are generally present from about 0.5% to 30%, preferably from about 5% to 20% and generally appear in a ratio of solvent to polymer from about 10:1 to 1:1, more preferably from a ratio of about 8:1 to 2:1. Exact levels and ratios can be adjusted depending upon solvation, evaporation rate and the like.

The plasticizing solvent is chosen to provide for water co-solvency, suitable solubility regarding the polymer, low volatility, stability and of course safety (i.e., lack of toxicity). Thus the foundation employs safe solvents that provide little or no sensation of tackiness, or cooling (usually due to evaporation) on the applied area. For example, any of the glycols is contemplated to be useful, including polyethylene glycols. These solvents also can be dipolar aproptic solvents that minimize hydrogen bonding and concomitant gelling and the like. For example, DMSO or DMF would be acceptable solvents, but for the safety concerns with the solvents.

Typically the preferred polymer and plasticizing solvent are chosen such that the polymer and plasticizing solvent are in the aqueous phase of the emulsion. This diminishes any tacky sensation of polymer contacting the user's hands and fingers during the cosmetic's initial application. Typically the pigment is in the oil phase for evenness. The solvent is chosen for its slow evaporation rate and its presence in the aqueous phase, and solvation properties. Typically it also extends the workability of the foundation and delays any perceived onset of tackiness for as long as possible, preferably up to two minutes.

Other ingredients a) Pigments, colorants and fillers

There are no specific limitations as to the pigment, colorant or filler powders used in the foundation composition. Each may be a body pigment, inorganic white pigment inorganic colored pigment, pearling agent, and the like. Specific examples are talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, nylon powder, polyethylene powder, methacrylate powder, polystyrene powder, silk powder, crystalline cellulose, starch, titanated mica, iron oxide titanated mica, bismuth oxychloride, and the like. These pigments and powders can be used independently or in combination.

The pigments are typically used as opacifiers and colorants. They are present in a concentration sufficient to provide a pleasing color to the composition in the container in which the foundation is sold and to confer the desired coverage and color to skin when applied. These pigments can be used as treated particles, or as the raw pigments themselves. Typical pigment levels are selected for the particular purpose of the foundation. For example, a foundation for fair skinned individuals would typically use lighter pigments and those pigments in a lower amount, while a foundation for darker skinned individuals might require darker pigmentation and/or more pigmentation. Determination of these levels and pigment types is within the skill of the artisan. Pigments that are generally recognized as safe, and are listed in C.T.F.A. Cosmetic Ingredient Handbook, 3rd Ed., Cosmetic and Fragrance Assn., Inc., Washington D.C. (1982), incorporated herein by reference, are used.

It is preferred that the pigments are surface treated to provide added stability of color and ease of formulation. Hydrophobically treated pigments are more preferred, because they may be more easily dispersed in the oil phase. In addition, it may be useful to treat the pigments with a material that is compatible with that silicone phase. Particularly useful hydrophobic pigment treatments for use in water-in-silicone emulsions include polysiloxane treatments such as those disclosed in U.S. Pat. No. 5,143,722, incorporated herein by reference.

Filler powders can be used to modify the density, feel or thickness of the composition or as a matte finishing agent to hide skin defects and reduce shine. Such cosmetically acceptable agents include those disclosed in the C.T.F.A. Cosmetic Ingredient Handbook, 3rd Ed., Cosmetic and Fragrance Assn., Inc., Washington D.C. (1982), incorporated herein by reference. For example, spherical silica, hydrated silica, silicone-treated silica beads, mica, talc, polyethylene, bentonite, hectorite, kaolin, chalk, diatomaceous earth, attapulgite and the like may be utilized. Of the components useful as a matte finishing agents, low luster pigment, talc, polyethylene, hydrated silica, kaolin, titanium dioxide, titanated mica (mica coated with titanium dioxide) and mixtures thereof are preferred.

b) Emulsifiers

The hydrophilic-lipophilic balance value of the emulsifier (herein referred to as HLB) is chosen so as to provide a water-in-oil emulsion. This factor is referenced in Wilkinson and Moore, *Harry's Cosmeticology*, 7th Ed. 1982, p. 738, and Schick and Fowkes, Surfactant Science Series, Vol. 2, *Solvent Properties of Surfactant Solutions*, p 607, incorporated herein by reference. HLB values of surfactant emulsifiers for making water-in-oil emulsions are from about 3–6. These emulsifiers include those disclosed in the C.T.F.A. Cosmetic Ingredient Handbook, 3rd Ed., Cosmetic and Fragrance Assn., Inc., Washington D.C. (1982) pp. 587–592; and Remington's Pharmaceutical Sciences, 15th Ed. 1975, pp. 335–337; both incorporated herein by reference. These emulsifiers are known in the art, and mixtures of these can be used, including those in McCutcheon's Volume 1, *Emulsifiers & Detergents*, 1994, North American Edition, pp. 236–239; herein incorporated by reference.

Particularly useful emulsifiers for water-in-silicone emulsions include polydiorganosioxane-polyoxyalkylene copolymers. Such polymers are described in U.S. Pat. No. 4,268,499, incorporated herein by reference. Suitable copolymers are known and many are available commercially. A preferred emulsifier herein is known by its CTFA designation as dimethicone copolyol. Preferred emulsifiers are further disclosed by U.S. Pat. No. 5,143,722, incorporated herein by reference. The foundation may comprise from about 0.5% to about 10%, preferably from about 1% to about 5%, more preferably from about 1.5% to about 3% of one or more emulsifiers.

c. Waxes

Optionally, the foundation may contain one or more waxes to affect viscosity, feel or stability. Waxes are lower-melting organic mixtures or compounds of high molecular weight, solid at room temperature and generally similar in composition to fats and oils except that they contain no glycerides. They can be hydrocarbons, esters of fatty acids or alcohols. Waxes useful in the present invention are selected from the group consisting of animal waxes, vegetable waxes, mineral waxes, natural waxes, synthetic waxes, petroleum waxes, ethylenic polymers, hydrocarbons, silicone waxes, and mixtures thereof.

d. Moisturizers

Optionally, one or more moisturizing agents can be used in the foundation composition. Among the moisturizing agents useful in the foundation composition are such well known cosmetically effective moisturizing agents as glycerin, hydrogen starch hydrolysate, sorbitol, hydrolyzed silk and the like. These agents are defined in the C.T.F.A. Cosmetic Ingredient Handbook, 3rd Ed., Cosmetic and Fragrance Assn., Inc., Washington D.C. (1982), incorporated herein by reference.

e. Fragrances

In addition, a fragrance, is optionally present in the above foundation composition in a concentration to provide a light, pleasant scent during application or to mask any odors of the composition.

f. Preservatives

Typically preservatives, such as those listed in C.T.F.A. Cosmetic Ingredient Handbook, 3rd Ed., Cosmetic and Fragrance Assn., Inc., Washington D.C. (1982) pp. 575–580, incorporated herein by reference, are used in a foundation. The levels of these preservatives are readily determined by those skilled in the art. For example, favored levels are often less than 5% and typically less than 1%.

g. Miscellaneous Ingredients

Other material can be incorporated into the formulation without departing from the scope or spirit of the invention, for example, materials may be added to provide added stability at storage temperature, such as thickeners and the like, better feel upon application, such as waxes, increased viscosity, coloration when wet and the like.

Water dispersible and oil dispersible clays may be useful to thicken the water or the oil phase of the invention. The water dispersible clays comprise bentonite and hectorite, such as BENTONE EW, LT from Rheox; magnesium aluminum silicate, such as VEEGUM from Vanderbilt Co.; attapulgite such as ATTASORB or PHARMASORB from Engelhard, Inc.; laponite and montmorrilonite, such as GEL-WHITE from ECC America; and mixtures thereof. The oil dispersible clays comprise quaternium-18 bentonite, such as BENTONE 34 and 38 from Rheox; the CLAYTONE SERIES from ECC America; quaternium-18 hectorite, such as BENTONE GELS from Rheox; and mixtures thereof. Other particulate or organic thickeners may also be useful provided they do not compromise the function or aesthetics of the foundation.

Another optional component comprises one or more ultraviolet absorbing agents. Ultraviolet absorbing agents, often described as sunscreening agents, can be present in a concentration in the range of between about 1% and about 12% by weight, based on the total weight of composition.

Working Examples

Preferred examples of this film forming foundation are particularly concerned with the film forming polymers and their synergistic combination with cosolvents, to eliminate or alleviate the drawbacks present in the art. Thus examples shown herein below are illustrative and comparative, not exhaustive. Of course variations in the formulas can be and are contemplated; these variations are within the scope of the claims.

Typical methods used by the skilled artisan for formulating a conventional emulsion useful as a foundation are useful for preparing this foundation as well. There are several ways to prepare the foundation. However, preferred methods of processing may be more expeditious than others. The more preferred method is favored for processing purposes, and does not compromise any of the film forming foundation's characteristics.

For example, in preparing the aqueous phase, which contains the film forming polymer and plasticizing solvent, one can create a mixture of the polymer and plasticizing solvent and then add this mixture to the aqueous phase. Alternatively, the polymer can be added directly to the combined aqueous phase ingredients. If the polymer requires heating to dissolve, disperse or to speed preparation, one can heat the plasticizing solvent and the polymer to dissolve the polymer in the solvent and then add the mixture to the remaining aqueous phase ingredients. As another alternative, one heats the combined aqueous phase ingredients and then adds the polymer at a suitably high temperature to dissolve it. This order of addition is varied for processing convenience and expediency. It can be varied according to the particularities of the film forming polymer, formulation and batch size.

The following examples illustrate the invention, but are not intended to limit it in any way. Thus altering the examples, or even using altogether different materials which are within the scope of the claims is not outside of the contemplated invention. Hence the examples provided of the invention merely enable the skilled artisan to prepare and use it.

EXAMPLES

A standard foundation formulation was prepared for comparison testing. In these examples, a standard pigmented silicone phase was used. The small variation in the oil phase is not thought to alter the properties of the formulas. The polymer and cosolvent were varied in both type and level in the aqueous phase;

such as viscosity may be adjusted by amount and type of mixing as would be evident to one skilled in the art.

TESTING OF THE FOUNDATION

In-Vitro Abrasion Test

Films of foundation were cast on panels and allowed to dry. These dried films were then subjected to a controlled test for mechanical strength and abrasion resistance. In all cases, example compositions showed less visible damage and significantly lower removal from the substrate than the control composition.

Sensory Test

Several key sensory attributes define an acceptable foundation. These attributes provide an early measure of the consumer acceptance. Sensory testing was done under controlled temperature and humidity conditions. Test applications were randomized across panelists. At least 10 highly trained panelists participated in each blind, single use test. Thus, the following terms describe a foundation's general attributes, and are used herein to illustrate the invention's advantages over the art. These attributes fall into the three consumer concern areas discussed previously.

| Ingredient | Ex 1 | Ex 2 | Ex 3 | Ex 4 | Ex 5 | Ex 6 | Ex 7 | Comparative Example | Prior Art Control |
|---|---|---|---|---|---|---|---|---|---|
| Oil Phase | | | | | | | | | |
| Emulsifiers | 2.95 | 2.75 | 2.95 | 2.5 | 2.5 | 2.95 | 2.95 | 2.95 | 2.50 |
| non-volatile liquids | 5.00 | 5.00 | 5.00 | 5.00 | 2.00 | 5.00 | 5.00 | 5.00 | 2.00 |
| Volatile Silicones | 26.90 | 28.60 | 26.90 | 27.72 | 30.72 | 26.9 | 27.90 | 26.90 | 29.85 |
| Pigments and Fillers | 17.00 | 14.00 | 17.00 | 13.13 | 13.13 | 17.00 | 17.50 | 17.00 | 14.00 |
| Rheological Additives/ Fragrances/Preservatives | 1.00 | 1.00 | 1.00 | 1.00 | 1.00 | 1.00 | 1.00 | 1.00 | 1.00 |
| Aqueous Phase | | | | | | | | | |
| Deionized Water | 23.73 | 31.90 | 16.03 | 40.23 | 35.23 | 35.73 | 33.23 | 36.73 | 40.23 |
| Film forming polymer resin (1) | 5.00 | 2.50 | 7.50 | 2.00 | 5.00 | 1.00 | 2.00 | — | — |
| Propylene Carbonate | — | — | 15.00 | — | — | — | — | — | — |
| Dimethyl Isosorbide | — | 5.83 | — | — | — | — | — | — | — |
| Butylene Glycol | 10.00 | — | — | — | — | — | — | — | — |
| Methyl Paraben | 0.12 | 0.12 | 0.12 | 0.12 | 0.12 | 0.12 | 0.12 | 0.12 | 0.12 |
| Propylene Glycol | 8.00 | 8.00 | 8.00 | 8.00 | 8.00 | 8.00 | 8.00 | 8.00 | 8.00 |
| Citric Acid | — | — | 0.20 | — | — | — | — | — | — |
| Sodium Dehydroacetate | 0.30 | 0.30 | 0.30 | 0.30 | 0.30 | 0.30 | 0.30 | 0.30 | 0.30 |
| Sodium Chloride | — | — | — | — | 2.00 | 2.00 | 2.00 | 2.00 | 2.00 |
| Total | 100.00 | 100.00 | 100.00 | 100.00 | 100.00 | 100.00 | 100.00 | 100.00 | 100.00 |

| Ref | Ingredient Name | Supplier |
|---|---|---|
| 1 | DERMACRYL LT (example 4) | National Starch |
| 1 | VINEX 2019 (example 5) | Air Products |
| 1 | AQ-38S RESIN (example 1,2,3) | Eastman |
| 1 | PVP K-17 (example 6) | BASF |
| 1 | PVP/VA COPOLYMER (example 7) | ISP |

The examples were prepared by the following method:

Disperse pigments in silicone phase liquids using high speed disperser, high shear mill or other methods known in the art to ensure uniform color and efficient use of pigment. Add the remainder of the ingredients in the silicone phase and sheer until well mixed, heating if necessary to ensure any solid waxes are melted. Combine all aqueous phase ingredients, (except polymer), with mixing. Add the polymers to the aqueous phase using methods described in their supplier's literature. Cool both phases to room temperature and slowly add the aqueous phase to the silicone phase, mixing with stirrer, homogenizer or other methods known in the art to form an emulsion. Final properties of the emulsion 1) Look Evenness—The degree to which the material spreads evenly over the skin, as determined by the appearance during/after the material is spread on the skin.

Blendability—The degree to which the foundation blends easily onto itself during re-application, shown visually.

2) Feel

Spreadability—The ease with which the foundation spreads onto the skin during application. Typically it is measured just after the start of application and describes the force it takes to move or spread the foundation. It often describes "when" the consumer should stop spreading the foundation.

Slipperiness—This parameter describes the perceived slipperiness or slickness of the foundation on the skin during manipulation.

Playtime—The amount of time needed to manipulate the foundation on the face to provide the desired effect (i.e., the length of time that the foundation can be manipulated).

Residue—The amount of residue left on the skin. If too much residue is left on the skin the foundation feels and appears to be applied too heavily, and it can feel "heavy" or thick. This attribute is easily measured by touch. For example, a "pancake" make-up used in theaters is considered very heavy.

Tackiness—This feeling can last beyond application of the foundation, and is a sticky, damp feel on the surface of the skin while applying the foundation.

Sensory information was collected to test the invention against prior art products, determine perceived product similarities or differences and provide understanding the effects of formulation manipulations.

The sensory performance is better than most prior art film forming formulations, with applications, look and feel attributes similar to the non-film forming foundations on the whole. Thus the cosmetic is quite acceptable.

Wear Panel Testing

Because of the special challenges of preparing a good "whole face" foundation, examples of the invention were evaluated. Feel and look were evaluated as well as wear. Wear attributes such as retention of the "freshly applied" look, shine control, original color (lack of "bleeding of color" over time), flawlessness, and lightness on the skin over time were evaluated.

The invention was tested using different polymers and solvents at various levels. In an in-house test, a panel assessed the wear and application properties of the prior art non-film forming foundation against the invention. The panel consisted of 16 females that currently use foundation a minimum of five times per week, have fair complexions, wear make-up for a minimum of five hours each day and notice application differences and appearance differences and changes in appearance throughout the day.

The product was applied to the face. The foundation was evaluated. After application, the foundation was worn under normal conditions for 5 hours, and the foundation was reevaluated for wear and appearance of the foundation. Upon reevaluation, the overall opinion of the foundation's wear performance was judged in terms of its look (coverage, "freshness," shine control, lack of bleeding, feeling light on the skin).

In addition, photographs of the face were taken after application and again after five hours wear. The images were assessed by expert graders for wear performance The invention was judged superior to the prior art control based on panelist responses or expert visual assessment.

Having described how to make and use the invention, we distinctly and specifically define the invention herein below:

What is claimed is:

1. A film forming foundation emulsion composition comprising an internal aqueous phase and an external oil phase, wherein the aqueous internal phase comprises:
   a. from about 0.5% to about 10% by weight of said composition, of water soluble or dispersible film forming polymer capable of forming a thin elastomeric film that physically adheres or interacts with the skin and is removable with water, said film forming polymer being selected from the group consisting of sulfopolyester resins, water dispersible, non-crosslinked acrylic resins, polyvinylacetate/polyvinyl alcohol resins, polyvinyl pyrrolidone (PVP), PVP/VA copolymers and mixtures of said film forming polymers; and
   b. from about 0.5% to about 35% by weight of said composition of one or more slow evaporating, water miscible or dispersible plasticizing solvent(s) selected from the group consisting of propylene glycol phenyl ether, propylene glycol, butylene glycol, hexylene glycol, dipropylene glycol, glycerol, dipropylene glycol methyl ether, polyethylene glycol 4, polyethylene glycol 8, propylene carbonate, and dimethyl isosorbide, wherein the emulsion is a water-in-oil emulsion.

2. A foundation according to claim 1, wherein the solvent is selected from the group consisting of butylene glycol, propylene carbonate, propylene glycol, dimethyl isosorbide, and mixtures thereof.

3. A foundation according to claim 2, wherein the film forming polymer is selected from the group consisting of acrylates/octylacrylamide copolymers, digylcol/CHDM/isophthalates/SIP copolymers, PVP, PVP/VA copolymers and mixtures of said film forming polymers.

4. A foundation according to claim 3 wherein the polymer is present in an amount of about 1% to about 8% by weight of the composition.

5. A foundation according to claim 4, wherein the polymer is selected from the group consisting of diglycol/CHDM/isophathalates/SIP copolymers, PVP and mixtures thereof.

6. A foundation according to claim 5, wherein the solvent is selected from the group consisting of butylene glycol, propylene glycol and mixtures thereof.

7. A foundation according to claim 5, wherein the solvent is selected from the group consisting of propylene carbonate, propylene glycol and mixtures thereof.

8. A foundation according to claim 5, wherein the solvent is propylene glycol.

9. A foundation according to claim 5 wherein the polymer is present in an amount of from about 1% to about 5% by weight and the polymer is PVP.

10. A film forming foundation emulsion composition comprising an internal aqueous phase and an external oil phase, wherein the aqueous internal phase comprises:
   a. from about 0.5% to about 10% by weight of said composition, of water soluble or dispersible film forming polymer capable of forming a thin elastomeric film that physically adheres or interacts with the skin and is removable with water, said film forming polymer being selected from the group consisting of sulfopolyester resins, water dispersible, non-crosslinked acrylic resins, polyvinylacetate/polyvinyl alcohol resins, polyvinyl pyrrolidone (PVP), PVP/VA copolymers and mixtures of said film forming polymers; and
   b. from about 0.5% to about 35% by weight of said composition of one or more slow evaporating, water miscible or dispersible plasticizing solvent(s) selected from the group consisting of propylene glycol phenyl ether, propylene glycol, butylene glycol, hexylene glycol, dipropylene glycol, glycerol, dipropylene glycol methyl ether, polyethylene glycol 4, polyethylene glycol 8, propylene carbonate, and dimethyl isosorbide, wherein the emulsion is a water-in-silicone emulsion.

11. A foundation according to claim 10 wherein the solvent is selected from the group consisting of butylene glycol, propylene carbonate, propylene glycol, dimethyl isosorbide, and mixtures thereof.

12. A foundation according to claim 11 wherein the film forming polymer is selected from the group consisting of acrylates/octylacrylamide copolymers, diglycol/CHDM/isophthalates/SIP copolymers, PVP, PVP/VA copolymers and mixtures of said film forming polymers.

13. A foundation according to claim 12 wherein the film forming polymer is present in an amount of about 1% to about 8% by weight of the composition.

14. A foundation according to claim 13 wherein the polymer is selected from the group consisting of a diglycol/ CHDM/isophthalates/SIP copolymers, PVP, PVP/VA copolymers and mixtures of said polymers.

15. A foundation according to claim 14 wherein the solvent is selected from the group consisting of butylene glycol, propylene glycol and mixtures thereof.

16. A foundation according to claim 14 wherein the solvent is selected from the group consisting of propylene carbonate, propylene glycol and mixtures thereof.

17. A foundation according to claim 14 wherein the solvent is propylene glycol.

18. A foundation according to claim 14 wherein the polymer is present in an amount of from about 1% to about 5% by weight of the composition and the polymer is PVP.

* * * * *

UNITED STATES PATENT AND TRADEMARK OFFICE
CERTIFICATE OF CORRECTION

PATENT NO. : 6,060,547
DATED : May 9, 2000
INVENTOR(S) : Canter et al.

It is certified that error appears in the above-identified patent and that said Letters Patent is hereby corrected as shown below:

Column 1,
Line 55, "pigment" should read -- pigmented --.
Line 56, "to pleasant" should read -- or pleasant --.

Column 2,
Line 28, "then" should read -- than --.
Line 37, "an" should read -- a --.

Column 3,
Line 26, omit "(Acrylates/Octylacrylamide Copolymer)".
Line 45, "of" should read -- or --.

Column 6,
Line 18, "Electrical" should read -- Electric --.
Line 24, "silicon" should read -- silicone --.

Column 8,
Line 11, "aproptic" should read -- aprotic --.

Column 9,
Line 34, "polydiorgansioxane" should read -- polydiorgansiloxane --.

Column 13,
Line 21, "applications" should read -- application --.

Column 14,
Line 55, omit "glycerol,".

Signed and Sealed this

Twenty-third Day of October, 2001

Attest:

*Nicholas P. Godici*

NICHOLAS P. GODICI
Attesting Officer   Acting Director of the United States Patent and Trademark Office